(12) United States Patent
Koh et al.

(10) Patent No.: US 10,113,191 B2
(45) Date of Patent: Oct. 30, 2018

(54) MICROORGANISMS HAVING ENHANCED L-AMINO ACIDS PRODUCTIVITY AND PROCESS FOR PRODUCING L-AMINO ACIDS USING THE SAME

(71) Applicant: CJ CHEILJEDANG CORPORATION, Seoul (KR)

(72) Inventors: Eun Sung Koh, Suwon-si (KR); Su Yon Kwon, Seoul (KR); Kwang Ho Lee, Seoul (KR); Ji Sun Lee, Incheon (KR); Juno Jang, Seoul (KR); Keun Cheol Lee, Hwaseong-si (KR); Hyeong Pyo Hong, Gangneung-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/112,855

(22) PCT Filed: Mar. 17, 2015

(86) PCT No.: PCT/KR2015/002551
§ 371 (c)(1),
(2) Date: Jul. 20, 2016

(87) PCT Pub. No.: WO2015/142021
PCT Pub. Date: Sep. 24, 2015

(65) Prior Publication Data
US 2017/0002388 A1    Jan. 5, 2017

(30) Foreign Application Priority Data
Mar. 21, 2014 (KR) ........................ 10-2014-0033698

(51) Int. Cl.
| | |
|---|---|
| *C12P 13/22* | (2006.01) |
| *C12N 9/24* | (2006.01) |
| *C12N 9/78* | (2006.01) |
| *C12P 13/08* | (2006.01) |

(52) U.S. Cl.
CPC .......... *C12P 13/227* (2013.01); *C12N 9/2497* (2013.01); *C12N 9/78* (2013.01); *C12P 13/08* (2013.01); *C12Y 302/02004* (2013.01); *C12Y 305/04004* (2013.01)

(58) Field of Classification Search
None
See application file for complete search history.

(56) References Cited

U.S. PATENT DOCUMENTS

| | | | | |
|---|---|---|---|---|
| 7,527,950 | B2 * | 5/2009 | Livshits | C07K 14/245 435/106 |
| 8,309,329 | B2 | 11/2012 | Asahara et al. | |
| 2007/0161090 | A1 | 7/2007 | Matsui et al. | |
| 2013/0040347 | A1 | 2/2013 | Lee et al. | |
| 2015/0050703 | A1 | 2/2015 | Cheong et al. | |

FOREIGN PATENT DOCUMENTS

| | | |
|---|---|---|
| EP | 2233570 | 9/2010 |
| WO | 0009660 A1 | 2/2000 |
| WO | 02097086 | 12/2002 |
| WO | 2008082179 A1 | 7/2008 |
| WO | 2012099396 | 7/2012 |
| WO | 2013103268 A2 | 7/2013 |

OTHER PUBLICATIONS

Ishida et al., "Factors Improving L-Threonine Production by a Three L-Threonine Biosynthetic Genes-amplified Recombinant Strain of Brevihacterium lactofermentum", Biosci. Biotech. Biochem., 1994, 58 (4):768-770.*
Morrison et al., "An AMP nucleosidase gene knockout in *Escherichia coli* elevates intracellular ATP levels and increases cold tolerance", Biol. Lett. (2008) 4, 53-56. doi:10.1098/rsbl.2007.0432.*
Kaleta et al., "Metabolic costs of amino acid and protein production in *Escherichia*" Biotechnology Journal, Sep. 2013, 8(9):1105-114.*
Adenosine Deaminase [*Escherichia coli* B354], Posted Mar. 24, 2010, p. 1, Retrieved from the Internet Jun. 3, 2015 <URL:http://www.ncbi.nlm.nih.gov/protein/291470400?sat=16&satkey=8261594>.
AMP nucleosidase [*Escherichia coli* MS 84-1], Posted Jun. 6, 2013, pp. 1-2, Retrieved from the Internet Jun. 3, 2015 <URL:http://www.ncbi.nlm.nih.gov/protein/300405911?report=genbank&log$=protalign&b . . . >.
International Search Report—Application No. PCT/KR2015/002551 dated Jun. 9, 2015.
Taiwan Office Action—Taiwan Application No. 104108792 dated Oct. 26, 2015.
UniProtKB-C8UCL4 (C8UCL4_ECO1A), pp. 1-6, Retrieved from the Internet Oct. 23, 2015 <URL:www.uniprot.org/uniprot/C8UCL4>.
Written Opinion—Application No. PCT/KR2015/002551 dated Jun. 9, 2015.
Jun Lin et al., Enhancement of glutathione production in a coupled system of adenosine deaminase-deficient recombinant *Escherichia coli* and *Saccharomyces cerevisiae*, 2009, p. 269-273, vol. 44, Enzyme and Microbial Technology.
Japanese Office Action for Application No. 2016549396 dated May 30, 2017.
Kiyotaka Y. Hara, et al., "Systematic genome-wide scanning for genes involved in ATP generation in *Escherichia coli*", Metabolic Engineering 11 (2009) 1-7.

* cited by examiner

*Primary Examiner* — Suzanne M Noakes
(74) *Attorney, Agent, or Firm* — Cantor Colburn LLP

(57) ABSTRACT

Disclosed are a recombinant microorganism having enhanced L-amino acid productivity, wherein the recombinant microorganism is transformed to have removed or decreased activity of at least one of adenosine deaminase and AMP nucleosidase, and a method of producing an L-amino acid using the recombinant microorganism. The use of the recombinant microorganism may enable the production of the L-amino acid in a highly efficient manner.

11 Claims, 1 Drawing Sheet
Specification includes a Sequence Listing.

SEQUENCE LISTING

<160> NUMBER OF SEQ ID NOS: 16

<210> SEQ ID NO 1
<211> LENGTH: 70
<212> TYPE: DNA
<213> ORGANISM: Artificial Sequence
<220> FEATURE:
<223> OTHER INFORMATION: primer

<400> SEQUENCE: 1

```
caacattcgt ccccagacca ttcttgaact tggccgccag tataatatct aggtgacact    60
atagaacgcg                                                           70

<210> SEQ ID NO 2
<211> LENGTH: 70
<212> TYPE: DNA
<213> ORGANISM: Artificial Sequence
<220> FEATURE:
<223> OTHER INFORMATION: primer

<400> SEQUENCE: 2
ggaaagccat ttccagacca ttaatctgtg cctggcggat ttgctcgcgg tagtggatct    60
gatgggtacc                                                           70

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
atgattgata ccaccctgcc attaactgat atccatcgcc accttgatgg caacattcgt    60
ccccagacca                                                           70

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4
ttacttcgcg gcgactttt ctcgcagtgc gcgttttcc tcagcgctga ggaaagccat     60
ttccagacca                                                           70

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
tgtggctgga ttaattaacg ccatcc                                         26

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gcgcgacttt gtgccttgca tg                                             22

<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
```

```
agcctggcga agatcatccg atcttcgcct tacacttttg tttcacattt ctgtgacata      60
ctatcggatg                                                             70
```

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8

```
gaaatagcgc cttcataaaa acggttagcc tggccgggaa gtttaatctc gccatgcaac      60
ggtttatctg                                                             70
```

<210> SEQ ID NO 9
<211> LENGTH: 70
<212> TYPE: DNA
<213> ORGANISM: Artificial Sequence
<220> FEATURE:
<223> OTHER INFORMATION: primer

<400> SEQUENCE: 9

```
ctgtgacata ctatcggatg tgcggtaatt gtatggaaca ggagacacac aggtgacact      60
atagaacgcg                                                             70
```

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10

```
gccatgcaac ggtttatctg aaacacacag tagtgtcccg tatggcacgc tagtggatct      60
gatgggtacc                                                             70
```

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11

```
cattgcgcat gacatggtgg t                                                21
```

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12

```
gtgcctgctt tgcacgttca a                                                21
```

<210> SEQ ID NO 13
<211> LENGTH: 1002
<212> TYPE: DNA
<213> ORGANISM: E.coli
<220> FEATURE:
<221> NAME/KEY: gene
<222> LOCATION: (1)..(1002)

<223> OTHER INFORMATION: add

<400> SEQUENCE: 13

```
atgattgata ccaccctgcc attaactgat atccatcgcc accttgatgg caacattcgt      60
ccccagacca ttcttgaact tggccgccag tataatatct cgcttcctgc acaatccctg     120
gaaacactga ttccccacgt tcaggtcatt gccaacgaac ccgatctggt gagctttctg     180
accaaacttg actggggcgt taaagttctc gcctctcttg atgcctgtcg ccgcgtggca     240
tttgaaaaca ttgaagatgc agcccgtcac ggcctgcact atgtcgagct gcgttttca     300
ccaggctaca tggcaatggc acatcagctg cctgtagcgg tgttgtcga agcggtgatc     360
gatggcgtac gtgaaggttg ccgcacctt ggtgtgcagg cgaagcttat cggcattatg      420
agccggacct tcggcgaagc cgcctgtcag caagagctgg aggccttttt agcccaccgt     480
gaccagatta ccgcacttga tttagccggt gatgaacttg gtttcccggg aagtctgttc     540
ctttctcact tcaaccgcgc gcgtgatgcg ggctggcata ttaccgtcca tgcaggcgaa     600
gctgccgggc cggaaagcat ctggcaggcg attcgtgaac tgggtgcgga gcgtattgga     660
catggcgtaa aagccattga agatcgggcg ctgatggatt ttctcgccga gcaacaaatt     720
ggtattgaat cctgtctgac ctccaatatt cagaccagca ccgtagcaga gctggctgca     780
catccgctga aaacgttcct tgagcatggc attcgtgcca gcattaacac tgacgatccc     840
ggcgtacagg gagtggatat cattcacgaa ataccgttg ccgcgccagc tgctgggtta      900
tcccgcgagc aaatccgcca ggcacagatt aatggtctgg aaatggcttt cctcagcgct     960
gaggaaaaac gcgcactgcg agaaaaagtc gccgcgaagt aa                       1002
```

<210> SEQ ID NO 14
<211> LENGTH: 333
<212> TYPE: PRT
<213> ORGANISM: E.coli

<400> SEQUENCE: 14

```
Met Ile Asp Thr Thr Leu Pro Leu Thr Asp Ile His Arg His Leu Asp
  1               5                  10                  15

Gly Asn Ile Arg Pro Gln Thr Ile Leu Glu Leu Gly Arg Gln Tyr Asn
             20                  25                  30

Ile Ser Leu Pro Ala Gln Ser Leu Glu Thr Leu Ile Pro His Val Gln
         35                  40                  45

Val Ile Ala Asn Glu Pro Asp Leu Val Ser Phe Leu Thr Lys Leu Asp
     50                  55                  60

Trp Gly Val Lys Val Leu Ala Ser Leu Asp Ala Cys Arg Arg Val Ala
 65                  70                  75                  80

Phe Glu Asn Ile Glu Asp Ala Ala Arg His Gly Leu His Tyr Val Glu
                 85                  90                  95

Leu Arg Phe Ser Pro Gly Tyr Met Ala Met Ala His Gln Leu Pro Val
            100                 105                 110

Ala Gly Val Val Glu Ala Val Ile Asp Gly Val Arg Glu Gly Cys Arg
        115                 120                 125

Thr Phe Gly Val Gln Ala Lys Leu Ile Gly Ile Met Ser Arg Thr Phe
    130                 135                 140

Gly Glu Ala Ala Cys Gln Gln Glu Leu Glu Ala Phe Leu Ala His Arg
145                 150                 155                 160

Asp Gln Ile Thr Ala Leu Asp Leu Ala Gly Asp Glu Leu Gly Phe Pro
                165                 170                 175
```

```
Gly Ser Leu Phe Leu Ser His Phe Asn Arg Ala Arg Asp Ala Gly Trp
            180                 185                 190
His Ile Thr Val His Ala Gly Glu Ala Ala Gly Pro Glu Ser Ile Trp
        195                 200                 205
Gln Ala Ile Arg Glu Leu Gly Ala Glu Arg Ile Gly His Gly Val Lys
    210                 215                 220
Ala Ile Glu Asp Arg Ala Leu Met Asp Phe Leu Ala Glu Gln Gln Ile
225                 230                 235                 240
Gly Ile Glu Ser Cys Leu Thr Ser Asn Ile Gln Thr Ser Thr Val Ala
                245                 250                 255
Glu Leu Ala Ala His Pro Leu Lys Thr Phe Leu Glu His Gly Ile Arg
            260                 265                 270
Ala Ser Ile Asn Thr Asp Asp Pro Gly Val Gln Gly Val Asp Ile Ile
        275                 280                 285
His Glu Tyr Thr Val Ala Ala Pro Ala Ala Gly Leu Ser Arg Glu Gln
    290                 295                 300
Ile Arg Gln Ala Gln Ile Asn Gly Leu Glu Met Ala Phe Leu Ser Ala
305                 310                 315                 320
Glu Glu Lys Arg Ala Leu Arg Glu Lys Val Ala Ala Lys
                325                 330

<210> SEQ ID NO 15
<211> LENGTH: 1455
<212> TYPE: DNA
<213> ORGANISM: E.coli
<220> FEATURE:
<221> NAME/KEY: gene
<222> LOCATION: (1)..(1455)
<223> OTHER INFORMATION: amn

<400> SEQUENCE: 15
atgaataata agggctccgg tctgacccca gctcaggcac tggataaact cgacgcgctg      60
tatgagcaat ctgtagtcgc attacgcaac gccattggca actatattac aagtggcgaa     120
ttacctgatg aaaacgcccg caaacaaggt cttttgtct atccatcact gaccgtaacc     180
tgggacggta gcacaaccaa tccccccaaa acgcgcgcat tggtcgcttt acccacgca     240
ggcagctaca ccaccacgat tactcgccct actctctttc gttcgtatct taatgaacaa     300
cttacgttgc tgtatcagga ttatggtgcg catatctcag tgcaaccctc gcagcatgaa     360
atcccttatc cttatgtcat cgatggctct gaattgacac ttgatcgctc aatgagcgct     420
gggttaactc gctacttccc gacaacagaa ctggcgcaaa ttggcgatga actgcagac     480
ggcatttatc atccaactga attctccccg ctatcgcatt tgatgcgcg ccgcgtcgat     540
tttccctcg cacggttgcg ccattatacc ggtacgccag ttgaacattt tcagccgttc     600
gtcttgttta ccaactacac acgttatgtg gatgaattcg ttcgttgggg atgcagccag     660
atcctcgatc ctgatagtcc ctacattgcc ctttcttgtg ctggcgggaa ctggatcacc     720
gccgaaaccg aagcgccaga agaagccatt tccgaccttg catggaaaaa acatcagatg     780
ccagcatggc atttaattac cgccgatggt cagggtatta ctctggtgaa tattggcgtg     840
ggaccgtcaa atgctaaaac catctgcgat catctggcag tgctacgccc ggatgtctgg     900
ttgatgattg gtcactgtgg cggattacgt gaaagtcagg ccattggcga ttatgtactt     960
gcacacgctt atttacgcga tgaccacgtt cttgatgcgg ttctgccgcc cgatattcct    1020
attccgagca ttgctgaagt gcaacgtgcg ctttatgacg ccaccaagct ggtgagcggc    1080
aggcccggtg aggaagtcaa acagcggcta cgtactggta ctgtggtaac cacagatgac    1140
```

```
aggaactggg aattacgtta ctcagcttct gcacttcgtt ttaacttaag ccgggccgta    1200
gcaattgata tggaaagtgc aaccattgcc gcgcaaggat atcgtttccg cgtgccatac    1260
gggacactac tgtgtgtttc agataaaccg ttgcatggcg agattaaact tcccggccag    1320
gctaaccgtt tttatgaagg cgctatttcc gaacatctgc aaattggcat tcgggcgatc    1380
gatttgctgc gcgcagaagg cgaccgactg cattcgcgta aattacgaac ctttaatgag    1440
ccgccgttcc gataa                                                     1455
```

<210> SEQ ID NO 16
<211> LENGTH: 484
<212> TYPE: PRT
<213> ORGANISM: E.coli

<400> SEQUENCE: 16

```
Met Asn Asn Lys Gly Ser Gly Leu Thr Pro Ala Gln Ala Leu Asp Lys
 1               5                  10                  15

Leu Asp Ala Leu Tyr Glu Gln Ser Val Val Ala Leu Arg Asn Ala Ile
            20                  25                  30

Gly Asn Tyr Ile Thr Ser Gly Glu Leu Pro Asp Glu Asn Ala Arg Lys
        35                  40                  45

Gln Gly Leu Phe Val Tyr Pro Ser Leu Thr Val Thr Trp Asp Gly Ser
    50                  55                  60

Thr Thr Asn Pro Pro Lys Thr Arg Ala Phe Gly Arg Phe Thr His Ala
65                  70                  75                  80

Gly Ser Tyr Thr Thr Ile Thr Arg Pro Thr Leu Phe Arg Ser Tyr
            85                  90                  95

Leu Asn Glu Gln Leu Thr Leu Leu Tyr Gln Asp Tyr Gly Ala His Ile
           100                 105                 110

Ser Val Gln Pro Ser Gln His Glu Ile Pro Tyr Pro Tyr Val Ile Asp
       115                 120                 125

Gly Ser Glu Leu Thr Leu Asp Arg Ser Met Ser Ala Gly Leu Thr Arg
   130                 135                 140

Tyr Phe Pro Thr Thr Glu Leu Ala Gln Ile Gly Asp Glu Thr Ala Asp
145                 150                 155                 160

Gly Ile Tyr His Pro Thr Glu Phe Ser Pro Leu Ser His Phe Asp Ala
                165                 170                 175

Arg Arg Val Asp Phe Ser Leu Ala Arg Leu Arg His Tyr Thr Gly Thr
            180                 185                 190

Pro Val Glu His Phe Gln Pro Phe Val Leu Phe Thr Asn Tyr Thr Arg
        195                 200                 205

Tyr Val Asp Glu Phe Val Arg Trp Gly Cys Ser Gln Ile Leu Asp Pro
    210                 215                 220

Asp Ser Pro Tyr Ile Ala Leu Ser Cys Ala Gly Gly Asn Trp Ile Thr
225                 230                 235                 240

Ala Glu Thr Glu Ala Pro Glu Glu Ala Ile Ser Asp Leu Ala Trp Lys
                245                 250                 255

Lys His Gln Met Pro Ala Trp His Leu Ile Thr Ala Asp Gly Gln Gly
            260                 265                 270

Ile Thr Leu Val Asn Ile Gly Val Gly Pro Ser Asn Ala Lys Thr Ile
        275                 280                 285

Cys Asp His Leu Ala Val Leu Arg Pro Asp Val Trp Leu Met Ile Gly
    290                 295                 300

His Cys Gly Gly Leu Arg Glu Ser Gln Ala Ile Gly Asp Tyr Val Leu
```

```
305                 310                 315                 320
Ala His Ala Tyr Leu Arg Asp Asp His Val Leu Asp Ala Val Leu Pro
                325                 330                 335

Pro Asp Ile Pro Ile Pro Ser Ile Ala Glu Val Gln Arg Ala Leu Tyr
                340                 345                 350

Asp Ala Thr Lys Leu Val Ser Gly Arg Pro Gly Glu Val Lys Gln
                355                 360                 365

Arg Leu Arg Thr Gly Thr Val Val Thr Thr Asp Asp Arg Asn Trp Glu
                370                 375                 380

Leu Arg Tyr Ser Ala Ser Ala Leu Arg Phe Asn Leu Ser Arg Ala Val
385                 390                 395                 400

Ala Ile Asp Met Glu Ser Ala Thr Ile Ala Ala Gln Gly Tyr Arg Phe
                405                 410                 415

Arg Val Pro Tyr Gly Thr Leu Leu Cys Val Ser Asp Lys Pro Leu His
                420                 425                 430

Gly Glu Ile Lys Leu Pro Gly Gln Ala Asn Arg Phe Tyr Glu Gly Ala
                435                 440                 445

Ile Ser Glu His Leu Gln Ile Gly Ile Arg Ala Ile Asp Leu Leu Arg
        450                 455                 460

Ala Glu Gly Asp Arg Leu His Ser Arg Lys Leu Arg Thr Phe Asn Glu
465                 470                 475                 480

Pro Pro Phe Arg
```

MICROORGANISMS HAVING ENHANCED L-AMINO ACIDS PRODUCTIVITY AND PROCESS FOR PRODUCING L-AMINO ACIDS USING THE SAME

TECHNICAL FIELD

The present invention relates to a microorganism having enhanced producibility of an L-amino acid and a method of producing an L-amino acid using the microorganism.

BACKGROUND ART

Adenosine-5'-triphosphate (ATP) has high-energy phosphate bonds and generate energy when ATP is hydrolyzed to adenosine diphosphate (ADP) and a phosphate. ATP is the main energy source for all living organisms. ATP is synthesized by electron transport system within a microorganism, substrate-level phosphorylation, or the like. The ATP supplies energy that is required by cells when being degraded, and then, is continuously recycled through a process of glycolysis or oxidative phosphorylation. In addition, microorganisms that produce useful metabolites by fermentation are known to demand for more ATP-like energies in accordance with the enhancement of ATP biosynthesis.

In this regard, the inventors of the present invention increase a proportion of the ATP, which is the most used energy source to produce an L-amino acid, within a cell, so as to confirm effects of the ATP on the production of the L-amino acid, thereby completing the present invention.

DETAILED DESCRIPTION OF THE INVENTION

Technical Problem

The present invention provides a recombinant microorganism having enhanced producibility of an L-amino acid in accordance with an increased ATP level therein.

The present invention provides a method of producing an L-amino acid using the recombinant microorganism.

Technical Solution

According to an aspect of the present invention, a recombinant microorganism having enhanced producibility of an L-amino acid is disclosed, wherein activity of at least one of adenosine deaminase and AMP nucleosidase is removed or decreased.

The term "adenosine deaminase (Add)" as used herein refers to an enzyme that is present in the cytosol and participates in a part of purine metabolism. The Add may act on a C-6 position of adenosine so that an amino group bound to the C-6 position is deaminated, and in this regard, the Add may have a role in catalyzing a conversion reaction of adenosine+$H_2O$→inosine+$NH_3$, resulting in production of inosine and ammonium.

An amino acid sequence of the Add may be provided by known data base, such as GenBank of NCBI, but the data base is not limited thereto. The Add may include, in detail, an amino acid sequence of SEQ ID NO: 14, or an amino acid sequence having about 80% or more, 90% or more, or 95% more sequence identity with the amino acid sequence of SEQ ID NO: 14. In addition, such an amino acid sequence having sequence identity includes an amino acid sequence in which a part of the sequence is deleted, modified, substituted, or added. The sequence of the Add may include a polynucleotide sequence encoding the amino acid sequence of SEQ ID NO: 14. The polynucleotide sequence encoding the Add protein may be referred as an add gene (NCBI Gene ID: 12931257). For example, a sequence of the add gene encoding the Add protein may include a polynucleotide sequence of SEQ ID NO: 13, or a polynucleotide sequence having about 80% or more, 90% or more, or 95% or more sequence identity with the polynucleotide sequence of SEQ ID NO: 13. Such a base sequence having sequence identity includes a base sequence in which a part of the sequence is deleted, modified, substituted, or added.

The term "AMP nucleosidase (Amn)" used herein refers to an enzyme that belongs to the family of hydrolases, e.g., glycosylases that hydrolyse N-glycosyl compounds, and is also called adenylate nucleosidase. The Amn may participate in a part of purine metabolism. For example, the Amn may have a role in catalyzing a conversion reaction of AMP+$H_2O$⇔ D-ribose 5-phosphate+adenine. In addition, when an amn gene encoding the Amn is inactivated, ATP levels within the cell may be increased.

An amino acid sequence of the Amn may be provided by known data base, such as GenBank of NCBI, but the data base is not limited thereto. The Amn may include, in detail, an amino acid sequence of SEQ ID NO: 16, or an amino acid sequence having about 80% or more, 90% or more, or 95% more sequence identity with the amino acid sequence of SEQ ID NO: 16. In addition, such an amino acid sequence having sequence identity includes an amino acid sequence in which a part of the sequence is deleted, modified, substituted, or added. The sequence of the Amn may include a polynucleotide sequence encoding the amino acid sequence of SEQ ID NO: 16. The polynucleotide sequence encoding the Amn protein may be referred as an amn gene (NCBI Gene ID: 12931407). For example, a sequence of the amn gene encoding the Amn protein may include a polynucleotide sequence of SEQ ID NO: 15, or a polynucleotide sequence having about 80% or more, 90% or more, or 95% or more sequence identity with the polynucleotide sequence of SEQ ID NO: 15. Such a base sequence having sequence identity includes a base sequence in which a part of the sequence is deleted, modified, substituted, or added.

In the present invention, the sequence identity refers to a degree of similarity in base sequences of genes encoding proteins or in amino acid sequences. In the case of high identity of genes, the expression products of the genes may have the same or similar activity as one another.

In the present invention, the activity of the Add or the Amn may be removed or decreased in a microorganism, and the microorganism may be used for the purpose of producing the L-amino acid. In the recombinant microorganism of the present invention having enhanced producibility of the L-amino acid, the activity of the Add and the Amn separately or together may be removed or decreased. For example, in the recombinant microorganism, the activity of both proteins may be removed or decreased. The recombinant microorganism having removed or decreased activity of the Add or the Amn results in enhanced producibility of the L-amino acid compared to a microorganism in which activity of the proteins is not removed or decreased.

The term "L-amino acid" as used herein refers to a basic structural unit of a protein constituting the body of an organism and having both an amino group and a carboxylic acid group that are attached to the same carbon atom. For example, the L-amino acid may be selected from the group consisting of L-leucine, L-phenylalanine, L-lysine, L-threonine, L-valine, L-isoleucine, L-tryptophan, and L-methionine. For example, the L-amino acid may be L-tryptophan or L-threonine.

The term "recombinant microorganism" as used herein refers to a microorganism that is genetically modified. The recombinant microorganism may be a microorganism that is genetically engineered, and for example, an exogenous nucleic acid may be introduced to a microorganism according to genetic engineering methods, or a sequence or location of an endogenous gene in a microorganism may be transformed.

The term "removed activity" of an enzyme or a polypeptide as used herein refers to a case where the above-described protein is not expressed at all in a microorganism, or a case where the above-described protein is expressed, but does not have any activity. The term "decreased activity" an enzyme or a polypeptide as used herein refers to a case where the above-described protein is expressed, but activity thereof is weak compared to the intrinsic activity. The term "removed activity" or "decreased activity" may be replaced with the term "inactivation" or "weakness of activity". The term "intrinsic activity" as used herein refers to activity of a microorganism in a natural state, i.e. activity originally existing in a microorganism, or activity of a protein that has not been genetically modified.

The removal or reduction of the activity of the Add or the Amn may be caused by removal or modification of genes that each encode the Add or the Amn. The term "removal or modification of genes" used herein refers to a case where a part or all of the genes or regulatory factors on promoter or terminator regions of the genes are mutated, substituted, deleted, or inserted with at least one base, so that the genes are not expressed or the genes are expressed in a small amount, or the genes are expressed without showing enzymatic activity or with decreased enzymatic activity. The removal or disruption of the genes may be achieved by genetic manipulation, such as homologous recombination, mutagenesis, or molecular evolution. When a cell includes a plurality of the same genes or at least two homologous genes of different polypeptides, one or more genes may be removed or disrupted in the cell. In an exemplary embodiment, the add gene encoding the Add or the amn gene encoding the Amn may be removed from the genome of the microorganism by homologous recombination, or may have a modified start codon.

The term "recombinant microorganism having enhanced producibility of the L-amino acid" as used herein refers to a microorganism capable of producing and accumulating the L-amino acid from a carbon source contained in a medium. The recombinant microorganism having removed or decreased activity of the Add or the Amn results in enhanced producibility of the L-amino acid compared to a microorganism in which activity of the enzymes is not modified. In an exemplary embodiment, it was confirmed that a threonine-producing strain and a tryptophan-producing strain that have inactivated enzymes described above each had enhanced producibility of threonine and tryptophan as compared to mother strains of the threonine-producing strain and the tryptophan-producing strain.

The recombinant microorganism may be a microorganism of the genus *Escherichia*, the genus *Enterbacter*, the genus *Erwinia*, the genus *Serratia*, the genus *Providencia*, the genus *Corynebacterium*, and the genus *Brevibacterium*. For example, the recombinant microorganism may be a microorganism of the genus *Escherichia*. The microorganism of the genus *Escherichia* may be *Escherichia coli* (*E. coli*), e.g., *E. coli* KCCM0000P. The *E. coli* KCCM0000P is a KCCM10910PΔaddΔamn strain prepared by using a threonine-producing strain (KCCM10910P) as a mother strain and performing deletion of both add and amn genes. Here, the production of threonine in the *E. coli* KCCM0000P is found to be greater than that in the mother strain (KCCM10910P).

The *E. coli* KCCM0000P was named 'CA03-8254P', and then, was deposited at the Korean Culture Center of Microorganisms (hereinafter, referred to as 'KCCM') on Dec. 9, 2013. under the Budapest Treaty. The *E. coli* KCCM0000P was given Accession Number KCCM11494P.

According to another aspect of the present invention, a composition for producing the L-amino acid is disclosed, wherein the composition includes the recombinant microorganism. The term "composition for producing the L-amino acid" as used herein refers to a composition capable of producing the L-amino acid as a metabolite using the recombinant microorganism producing the L-amino acid or a culture product of the recombinant microorganism. The recombinant microorganism producing the L-amino acid is defined the same as described above. The L-amino acid may be selected from the group consisting of, for example, L-leucine, L-phenylalanine, L-lysine, L-threonine, L-valine, L-isoleucine, L-tryptophan, and L-methionine. For example, the L-amino acid may be L-threonine or L-tryptophan. The term "culture product" as used herein refers to a broth culture containing the recombinant microorganism, a culture supernatant from which a microbial cell is removed, or a diluted solution of the culture product. The composition may further include an ingredient for increasing the productivity of the L-amino acid. For example, the composition may further include carbon sources, nitrogen sources, or trace element ingredients. The carbon sources may include, for example, carbohydrates, such as glucose, sucrose, lactose, fructose, maltose, starch, and cellulose; fats, such as soybean oil, sunflower oil, castor oil, and coconut oil; fatty acids, such as palmitic acid, stearic acid, and linoleic acid; alcohol, such as glycerol and ethanol; and organic acids, such as acetic acid, or a combination thereof. The culturing of the recombinant microorganism may be performed by using glucose as a carbon source. The nitrogen sources may include, for example, organic nitrogen sources, such as peptone, yeast extract, gravy, malt extract, corn steep liquor (CSL), and soybean flour; and inorganic nitrogen sources, such as urea, ammonium sulfate, ammonium chloride, ammonium phosphate, ammonium carbonate, and ammonium nitrate; or a combination thereof. The composition may include, as a phosphorus source, potassium dihydrogen phosphate or potassium hydrogen phosphate. In addition, the composition may include sodium-containing slats corresponding to the phosphorus source, and metal salts, such as magnesium sulfate or iron sulfate. In addition, a culture medium may include amino acids, vitamins, and appropriate precursors.

According to another aspect of the present invention, a method of producing the L-amino acid is disclosed, the method including: culturing the recombinant microorganism producing the L-amino acid; and collecting the L-amino acid from the culture product.

The recombinant microorganism producing the L-amino acid is defined the same as described above.

The L-amino acid may be selected from the group consisting of, for example L-leucine, L-phenylalanine, L-lysine, L-threonine, L-valine, L-isoleucine, L-tryptophan, and L-methionine. For example, the L-amino acid may be L-threonine or L-tryptophan. The culturing of the recombinant microorganism may be achieved in accordance with an appropriate culture medium and culture conditions that are well known in the art. In addition, one of ordinary skill in the art may appropriately adjust a culture medium and culture conditions according to the selected microorganism. The culture method may include a batch culture, a continuous culture, a fed-batch culture, or a combination thereof.

The culture medium may include a variety of carbon sources, nitrogen sources, and trace element ingredients. The carbon sources may include, for example, carbohydrates, such as glucose, sucrose, lactose, fructose, maltose, starch, and cellulose; fats, such as soybean oil, sunflower oil, castor oil, and coconut oil; fatty acids, such as palmitic acid, stearic acid, and linoleic acid; alcohol, such as glycerol and ethanol; and organic acids, such as acetic acid, or a combination thereof. The culturing of the recombinant microorganism may be performed by using glucose as a carbon source. The nitrogen sources may include, for example, organic nitrogen sources, such as peptone, yeast extract, gravy, malt extract, corn steep liquor (CSL), and soybean flour; and inorganic nitrogen sources, such as urea, ammonium sulfate, ammonium chloride, ammonium phosphate, ammonium carbonate, and ammonium nitrate; or a combination thereof. The culture medium may include, as a phosphorus source, potassium dihydrogen phosphate or potassium hydrogen phosphate. In addition, the culture medium may include sodium-containing slats corresponding to the phosphorus source, and metal salts, such as magnesium sulfate or iron sulfate. In addition, the culture medium may include amino acids, vitamins, and appropriate precursors. The medium or individual ingredients of the medium may be added to the culture medium in a batch or continuous manner.

In addition, compounds, such as ammonium hydroxide, potassium hydroxide, ammonia, phosphoric acid, and sulfuric acid may be added to the culture medium during the culturing of the recombinant microorganism in an appropriate manner, so as to adjust pH of the culture medium. In addition, antifoaming agents, such as fatty acid polyglycol ester, may be used during the culturing of the recombinant microorganism, so as to suppress production of air bubbles. In order to maintain aerobic conditions of the culture medium, oxygen or oxygen-containing gas (e.g., air) may be injected into the culture medium. Here, a temperature of the culture medium may typically be in a range of about 20° C. to about 45° C., for example, about 25° C. to about 40° C. A period of the culturing of the recombinant microorganism may last until a desired amount of the L-amino acid is obtained, and for example, the culturing of the recombinant microorganism may last about 10 hours to about 160 hours.

The collecting of the L-amino acid from the culture product may be performed by appropriate culture methods known in the art, such as a batch culture, a continuous culture, or a fed-batch culture, so as to collect or recover the L-amino acid produced in the culture product.

Advantageous Effects of the Invention

According to an aspect, a microorganism having removed or decreased activity of at least one protein selected from adenosine deaminase and AMP nucleosidase may be used to produce an L-amino acid.

According to another aspect, a composition for producing an L-amino acid or a method of producing an L-amino acid may be used to produce an L-amino acid in an efficient manner.

MODE OF THE INVENTION

Figure 1:
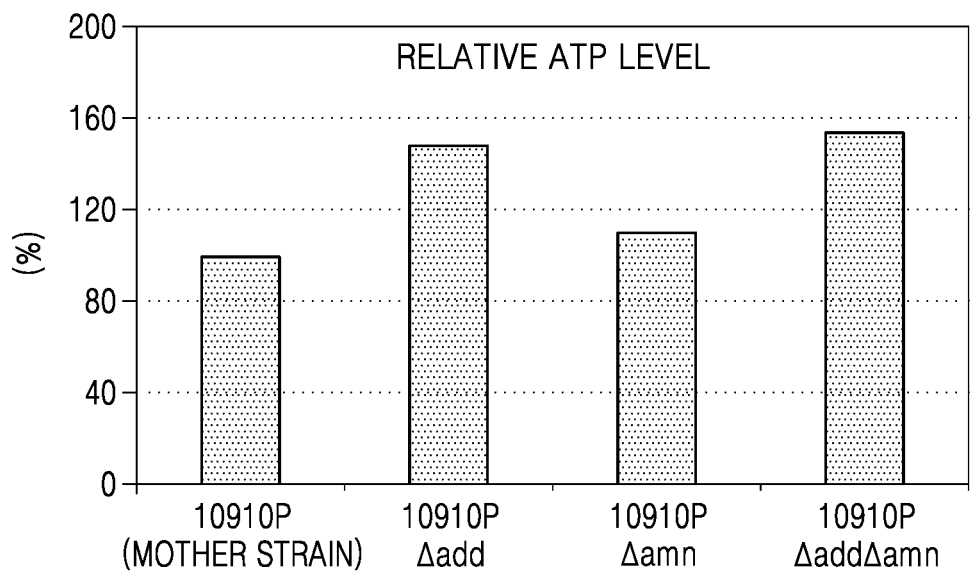
FIG. 1 is a graph showing ATP levels in an L-threonine-producing strain upon gene deletion performed according to the present invention.

Hereinafter, the present invention will be described in further detail with reference to the following examples. These examples are for illustrative purposes only and are not intended to limit the scope of the present invention.

Example 1: Preparation of L-Threonine-Producing Strain and L-Tryptophane-Producing Strain, Each has Weakened Activity of a Protein Encoded by Add Gene or Amn Gene In L-threonine-producing strains, i.e., KCICM10910P (Korean Patent No: 2009-0076389) and KCCM-10132 (Korean Patent NO: 2000-0013853), and L-tryptophane-producing strain, i.e., KCCM10812P (Korean Patent Publication No: 10-0792095), genes that each encode the Add and the Amn were deleted by homologous recombination. The add and amn genes to be deleted each include a base sequence of SEQ ID NO: 13 and a base sequence of SEQ ID NO: 15.

In detail, one step inactivation, which is a technique of constructing a mutant using lambda Red recombinase developed by Datsenko K A et al. (Proc Natl Acad Sci USA., (2000) 97:6640-6645), was used. To confirm the insertion of amplification product into the gene, a chloramphenicol-resistant gene of pUCprmfmloxC was used as a marker (Korean Patent No: 2009-007554). Then, polymerase chain reaction (hereinafter, referred to as "PCR") was performed by using pUCprmfmloxC as a template, a primer set of SEQ ID NOS: 1 and 2 having a part of the base sequences of these two genes and a part of the base sequence of the chloramphenicol-resistant gene of pUCprmfmloxC, and a primer set of SEQ ID NOS: 7 and 8 under the following conditions: 30 cycles of denaturation at 94° C. for 30 seconds, annealing at 55° C. for 30 seconds, and elongation at 72° C. for 1 minute, resulting in the amplification of a gene fragment of approximately 1,200 bp.

The DNA fragment obtained by the PCR amplification was electrophoresed on a 0.8% agarose gel, eluted, and used as a template for secondary PCR. The secondary PCR was performed by using the eluted primary PCR product as a template, a primer set of SEQ ID NOS: 3 and 4 having 20 bp of a complementary sequence to the 5' and 3' regions of the primary DNA fragment and further having the 5' and 3' regions of the genes, a primer set of SEQ ID NOS: 9 and 10 under the following conditions: 30 cycles of denaturation at 94 ∟ for 30 seconds, annealing at 55 ∟ for 30 seconds, and elongation at 72∟ for 1 minute, resulting in the amplification of 4 types of a gene fragment of approximately 1,300 bp. The DNA fragments obtained therefrom were electrophoresed on a 0.8% agarose gel, eluted, and used in recombination.

E. coli, which was transformed with a pKD46 plasmid according to the method developed by Datsenko K A et al (Proc Natl Acad Sci USA., (2000) 97:6640-6645), was prepared as a competent strain, and transformation was performed by introducing the gene fragment of 1,300 bp that was obtained by PCR. The obtained strains were selected on a LB medium supplemented with chloramphenicol. Accordingly, a deletion of the genes was confirmed by a PCR product of approximately 1,440 bp and 2,104 bp obtained by PCR using a primer set of SEQ ID NOS: 5 and 6 and a primer set of SEQ ID NOS: 11 and 12.

After removal of the pKD46 plasmid, the primary recombinant *E. coli* strain having chloramphenicol resistance was introduced with a pJW168 plasmid so as to remove the chloramphenicol marker gene from the strain (Gene, (2000) 247,255-264). In the microbial cells that were finally obtained, a deletion of the genes was confirmed by a PCR product of approximately 340 bp and 1,004 bp obtained by PCR using a primer set of SEQ ID NOS: 5 and 6 and a primer set of SEQ ID NOS: 11 and 12.

A deletion of the amn gene was performed in the same manner as described above by using a strain where the add gene was deleted, a primer set of SEQ ID NOS: 5 and 6, and a primer set of SEQ ID NOS: 11 and 12, and accordingly, a double deletion of these two genes were confirmed.

According to the method described above, 6 types of L-threonine-producing strains, i.e., a KCCM10910PΔadd strain, a KCCM10910PΔamn strain, a KCCM10910PΔaddΔamn strain, a KCCM-10132Δadd strain, a KCCM-10132Δamn strain, and a KCCM-10132ΔaddΔamn strain, were prepared. In addition, 3 types of L-tryptophan-producing strains, i.e., a KCCM10812PΔadd strain, a KCCM10812PΔamn strain, and a KCCM10812PΔaddΔamn strain, were prepared.

Figure 2:
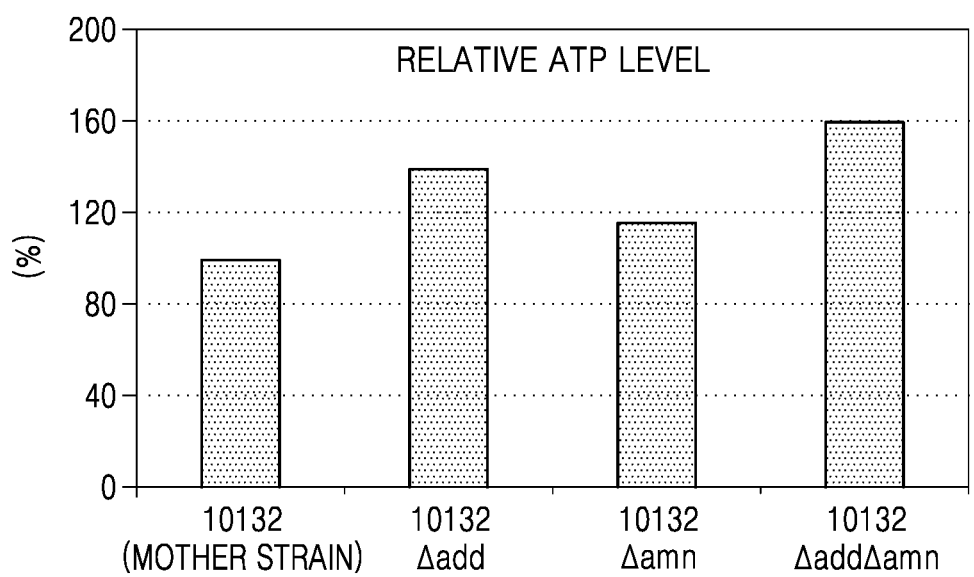
FIG. 2 is a graph showing ATP levels in an L-tryptophan-producing strain upon gene deletion performed according to the present invention.

Example 2. Measurement of ATP Levels in L-Threonine-Producing Strain and L-Tryptophan-Producing Strain In order to quantify actual ATP levels found in the strains of Example 1, the 'Efficient Method for Quantitative determination of Cellular ATP Synthetic Activity' developed by KIYOTAKA Y et al (J Biom Scre, (2006) V11: No. 3: PP310-17) in accordance with the use of luciferase was used. In a glucose-containing LB liquid medium, the strains of Example 1 each having different genetic transformation were cultured overnight. After removal of the supernatant by centrifugation, the microbial cells were washed with a solution of 100 mM Tris-Cl (pH 7.5), and then, treated with a permeable (PB) buffer solution (40%[v/v] Glucose, 0.8% [v/v] Triton X-100) for 30 minutes, thereby transporting the intracellular ATP to the outside. After separation of the supernatant by centrifugation again, the resultant was mixed with luciferin, which is used as a substrate of luciferase. After 10 minutes of a reaction, the degree of color development of the luciferase was measured by using a luminometer, so as to quantify ATP levels. The results are shown in FIGS. 1 and 2. All the resulting values were mean values obtained by experiments that were repeated 3 times.

As shown in FIGS. 1 and 2, in comparison between the mother strains without the gene deletion (i.e., the L-threonine-producing strain and the L-tryptophan-producing strain) and the strains of Example 1, it was confirmed that the ATP levels in the strains of Example 1 were found to be increased. In addition, it was confirmed that the ATP levels were further increased in the strains having the deletion of the add and amn genes in combinations rather than the strains having the deletion of a single gene.

Example 3. Confirmation of Effects of L-Threonine-Producing Strain Having Weakened Activity of Proteins Encoded by *E. coli* Add and Amn Genes in Glucose-Containing Medium In the L-threoine-producing strain (KCCM10910P) of Example 1, the add and amn genes were deleted separated or in combination, so as to proceed a potency test with respect to the strains having increased intracellular ATP levels by using glucose as a carbon source.

The strains each having different genetic transformation were cultured in the LB solid medium overnight in an incubation at 33° C. Afterwards, 1 platinum loop of each of the microbial cells was inoculated in 25 ml of titer medium containing glucose as shown in the composition of Table 1 below, and then, was cultured in an incubator at 33° C. and at 200 rpm for 50 hours. The results are shown in Table 2 below. All the resulting values were mean values obtained from 3 flasks.

TABLE 1

| Composition | Concentration (per liter) |
|---|---|
| Glucose | 70 g |
| $KH_2PO_4$ | 2 g |
| $(NH_4)_2SO_4$ | 25 g |
| $MgSO_4 \cdot H_2O$ | 1 g |
| $FeSO_4 \cdot H_2O$ | 5 mg |
| $MnSO_4 \cdot H_2O$ | 5 mg |
| Yeast extract | 2 g |
| Calcium carbonate | 30 g |
| pH | 6.8 |

TABLE 2

| Strain | OD | Glucose consumption (g/L)* | L-threonine (g/L)** |
|---|---|---|---|
| KCCM10910P | 25.8 | 30.3 | 31.5 |
| KCCM10910PΔadd | 23.7 | 33.9 | 32.7 |
| KCCM10910PΔamn | 22.9 | 35.7 | 33.4 |
| KCCM10910PΔaddΔamn | 22.7 | 36.0 | 33.6 |

*30-hr measured value
**50-hr measured value

As shown in Table 2 above, it was confirmed that the strains having the gene deletion according to the present invention resulted in the increased glucose consumption by about 18.8% as compared with the glucose consumption of the mother strain. It was also confirmed that the amounts of threonine produced in the strains were increased by about 6.6% as compared with the amount of threonine produced in the mother strain. These results denote that, in consideration of the ATP levels as shown in FIG. 1, the activity of the transformed strains was increased by the increased ATP levels thereof, and accordingly, the glucose consumption rates or the producibility of the amino acid of the transformed strains were improved.

In this regard, the *E. coli* KCCM10910PΔaddΔamn strain having enhanced glucose consumption rates and threonine producibility was named 'CA03-8254P' (Accession No: KCCM11494P, deposited at the Korean Culture Center of Microorganisms (KCCM) on Dec. 9, 2013).

Example 4. Confirmation of Effects of L-Threonine-Producing Strain Having Weakened Activity of Proteins Encoded by *E. coli* Add and Amn Genes in Glucose-Containing Medium In the L-threoine-producing strain (KCCM-10132) of Example 1, the add and amn genes were deleted separated or in combination, so as to proceed a potency test with respect to the strains having increased intracellular ATP levels by using glucose as a carbon source.

The strains each having different genetic transformation were cultured in the LB solid medium overnight in an incubation at 33° C. Afterwards, 1 platinum loop of each of the microbial cells was inoculated in 25 ml of titer medium containing glucose as shown in the composition of Table 1 below, and then, was cultured in an incubator at 33° C. and at 200 rpm for 50 hours. The results are shown in Table 3 below. All the resulting values were mean values obtained from 3 flasks.

TABLE 3

| Strain | OD | Glucose consumption (g/L)* | L-threonine (g/L)** |
|---|---|---|---|
| KCCM-10132 | 25.8 | 32.0 | 20.2 |
| KCCM-10132Δadd | 22.7 | 34.0 | 21.0 |
| KCCM-10132Δamn | 22.7 | 35.5 | 21.5 |
| KCCM-10132Δadd Δamn | 23.0 | 36.2 | 21.5 |

*30-hr measured value
**50-hr measured value

As shown in Table 3 above, it was confirmed that the strains having the gene deletion according to the present invention resulted in the increased glucose consumption by about 13% as compared with the glucose consumption of the mother strain. It was also confirmed that the amounts of threonine produced in the strains were increased by about 6.4% as compared with the amount of threonine produced in the mother strain.

Example 5. Confirmation of Effects of L-Tryptophan-Producing Strain Having Weakened Activity of Proteins Encoded by E. coli Add and Amn Genes in Glucose-Containing Medium In the L-tryptophan-producing strain (KCCM10812P) of Example 1, the add and amn genes were deleted separated or in combination, so as to proceed a potency test with respect to the strains having increased intracellular ATP levels by using glucose as a carbon source.

In order to proceed the potent test, 1 platinum loop of each of the microbial cells was inoculated in 25 ml of titer medium containing glucose as shown in the composition of Table 4 below, and then, was cultured in an incubator at 37° C. and at 200 rpm for 48 hours. The results are shown in Table 5 below. All the resulting values were mean values obtained from 3 flasks.

TABLE 4

| Composition | Concentration (per liter) |
|---|---|
| Glucose | 60 g |
| KH$_2$HPO$_4$ | 1 g |
| (NH$_4$)$_2$SO$_4$ | 10 g |
| NaCl | 1 g |
| MgSO$_4$•H$_2$O | 1 g |
| Sodium citrate | 5 g |
| Yeast extract | 2 g |
| Calcium carbonate | 40 g |
| Phenylalanine | 0.15 g |
| Thyrosine | 0.1 g |
| pH | 6.8 |

TABLE 5

| Strain | OD | Glucose consumption (g/L)* | L-tryptophan (g/L)** |
|---|---|---|---|
| KCCM10812P | 18.2 | 34.5 | 5.92 |
| KCCM10812PΔadd | 17.7 | 36.8 | 6.90 |
| KCCM10812PΔamn | 17.9 | 38.0 | 7.15 |
| KCCM10812PΔaddΔamn | 18.0 | 38.0 | 7.50 |

*33-hr measured value
**48-hr measured value

As shown in Table 5 above, it was confirmed that the strains having the gene deletion according to the present invention resulted in the increased glucose consumption by about 10% as compared with the glucose consumption of the mother strain. It was also confirmed that the amounts of tryptophan produced in the strains were increased by about 26.6% as compared with the amount of tryptophan produced in the mother strain. These results denote that, in consideration of the ATP levels as shown in FIG. 2, the activity of the transformed strains was increased by the increased ATP levels thereof, and accordingly, the glucose consumption rates or the producibility of the amino acid of the transformed strains were improved.

It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments of the present invention have been described with reference to the figures, it will be understood by those of ordinary skill in the art that various changes in form and details may be made therein without departing from the spirit and scope of the present invention as defined by the following claims.

[Accession number]
Depositary institution: Korean Culture Center of Microorganisms (international)
Accession number: KCCM11494P
Depositary date: Dec. 9, 2013

The invention claimed is:

1. A recombinant microorganism, wherein activity of at least one of adenosine deaminase comprising the amino acid sequence of SEQ ID NO: 14 and AMP nucleosidase comprising the amino acid sequence of SEQ ID NO: 16 is removed or decreased compared to that of a mother strain, wherein the recombinant microorganism belongs to the genus *Escherichia* and has enhanced producibility of an L-amino acid compared to that of the mother strain, wherein the L-amino acid is L-threonine or L-tryptophan, and wherein the recombinant microorganism does not contain chloramphenicol marker gene.

2. The recombinant microorganism of claim 1, wherein the recombinant microorganism is *Escherichia coli*.

3. The recombinant microorganism of claim 1, wherein activity of adenosine deaminase comprising the amino acid sequence of SEQ ID NO: 14 and AMP nucleosidase comprising the amino acid sequence of SEQ ID NO: 16 are removed or decreased compared to that of the mother strain.

4. The recombinant microorganism of claim 1, wherein at least one of a gene encoding adenosine deaminase comprising the amino acid sequence of SEQ ID NO: 14 and a gene encoding AMP nucleosidase comprising the amino acid sequence of SEQ ID NO: 16 is deleted or modified to be disrupted.

5. The recombinant microorganism of claim 4, wherein at least one of the genes is modified such that a part or all of the gene or regulatory factors on promoter or terminator regions of the genes are mutated, substituted, deleted, or inserted.

6. A method of producing L-amino acid, the method comprising:
culturing a recombinant microorganism; and
collecting an L-amino acid from the culture, wherein the L-amino acid is L-threonine or L-tryptophan,
wherein the recombinant microorganism has an activity of at least one of adenosine deaminase comprising the amino acid sequence of SEQ ID NO:14 and AMP nucleosidase comprising the amino acid sequence of SEQ ID NO:16 removed or decreased compared to that of a mother strain, does not contain chloramphenical marker gene, and has enhanced producibility of L-threonine or L-tryptophan compared to that of the mother strain.

7. The method of claim 6, wherein the recombinant microorganism is an *Escherichia*.

8. The method of claim 6, wherein the recombinant microorganism is an *Escherichia coli*.

9. The method of claim 6, wherein activity of adenosine deaminase comprising the amino acid sequence of SEQ ID NO: 14 and AMP nucleosidase comprising the amino acid sequence of SEQ ID NO: 16 in the recombinant microorganism are removed or decreased compared to that of the mother strain.

10. The method of claim 6, wherein at least one of a gene encoding adenosine deaminase comprising the amino acid sequence of SEQ ID NO: 14 and a gene encoding AMP nucleosidase comprising the amino acid sequence of SEQ ID NO: 16 in the recombinant microorganism is deleted or modified to be disrupted.

11. The method of claim 10, wherein at least one of the genes is modified such that a part or all of the genes or regulatory factors on promoter or terminator regions of the genes are mutated, substituted, deleted, or inserted.

* * * * *